(12) United States Patent
Lips et al.

(10) Patent No.: US 9,658,238 B2
(45) Date of Patent: May 23, 2017

(54) APPARATUS FOR PROCESSING BIOLOGICAL MATERIAL

(75) Inventors: Georg Lips, Feldmeilen (CH); Ulf Friederichs, Berg TG (CH)

(73) Assignee: QIAGEN GMBH, Hilden (DE)

( * ) Notice: Subject to any disclaimer, the term of this patent is extended or adjusted under 35 U.S.C. 154(b) by 1610 days.

(21) Appl. No.: 12/674,089

(22) PCT Filed: Aug. 20, 2008

(86) PCT No.: PCT/EP2008/060901
§ 371 (c)(1),
(2), (4) Date: Apr. 7, 2010

(87) PCT Pub. No.: WO2009/024587
PCT Pub. Date: Feb. 26, 2009

(65) Prior Publication Data
US 2011/0039709 A1    Feb. 17, 2011

(30) Foreign Application Priority Data
Aug. 20, 2007    (EP) .................................... 07016283

(51) Int. Cl.
G01N 35/04    (2006.01)
G01N 35/00    (2006.01)
G01N 33/50    (2006.01)

(52) U.S. Cl.
CPC ......... *G01N 35/04* (2013.01); *G01N 35/0099* (2013.01); *G01N 2035/0493* (2013.01)

(58) Field of Classification Search
CPC ............... G01N 35/04; G01N 35/0099; G01N 2035/0493
See application file for complete search history.

(56) References Cited

U.S. PATENT DOCUMENTS 6,457,642 B1 * 10/2002 Good et al. .............. 235/462.01

FOREIGN PATENT DOCUMENTS

EP    1243892    9/2002
GB    1352050    5/1974
(Continued)

OTHER PUBLICATIONS

International Search Report of PCT/EP2008/060901, completed Dec. 5, 2008.
(Continued)

*Primary Examiner* — Jeremy C Flinders
(74) *Attorney, Agent, or Firm* — McBee Moore Woodward & Vanik IP, LLC.

(57) ABSTRACT

The invention relates to an apparatus for purification, respectively processing and/or analysis of biological target molecules with a detection device for detecting at least one object, which includes at least one detection area, wherein the detection device is adapted to detect at least one height value of the detection area and is adapted to determine, from the at least one height value, a spatial position and/or orientation and/or a type and/or a presence and/or a number and/or a state of the at least one object. Further, the invention relates to a receiving device for receiving material for the processing, purification and/or analysis of biological target molecules with at least one identification element, wherein the at least one identification element defines a height profile for identifying the receiving device, wherein the height profile is provided for at least one height measurement and extends at least in sections along a line, preferably a straight line. Finally, the invention relates to a method for inventorying, position determining and/or orientation determining of objects, which are needed for the automatic processing of a material, which contains biological target molecules, on a corresponding apparatus, in which at least one height value (Continued)

of a detection area of the respective object is detected, and, from the height value, a spatial position and/or an orientation and/or a type and/or a presence and/or a number and/or a state of the respective object is determined on the apparatus.

52 Claims, 9 Drawing Sheets

(56) References Cited

FOREIGN PATENT DOCUMENTS

WO           2007039524      4/2007
WO    WO 2007039524 A2 *   4/2007

OTHER PUBLICATIONS

Communication about intention to grant a European patent in corresponding European Patent Application No. 08 787 349.3-1521 (4 pages).
English Language Specification and allowed Claims as Amended in corresponding European Patent Application No. 08 787 349.3-1521 (43 pages).

* cited by examiner

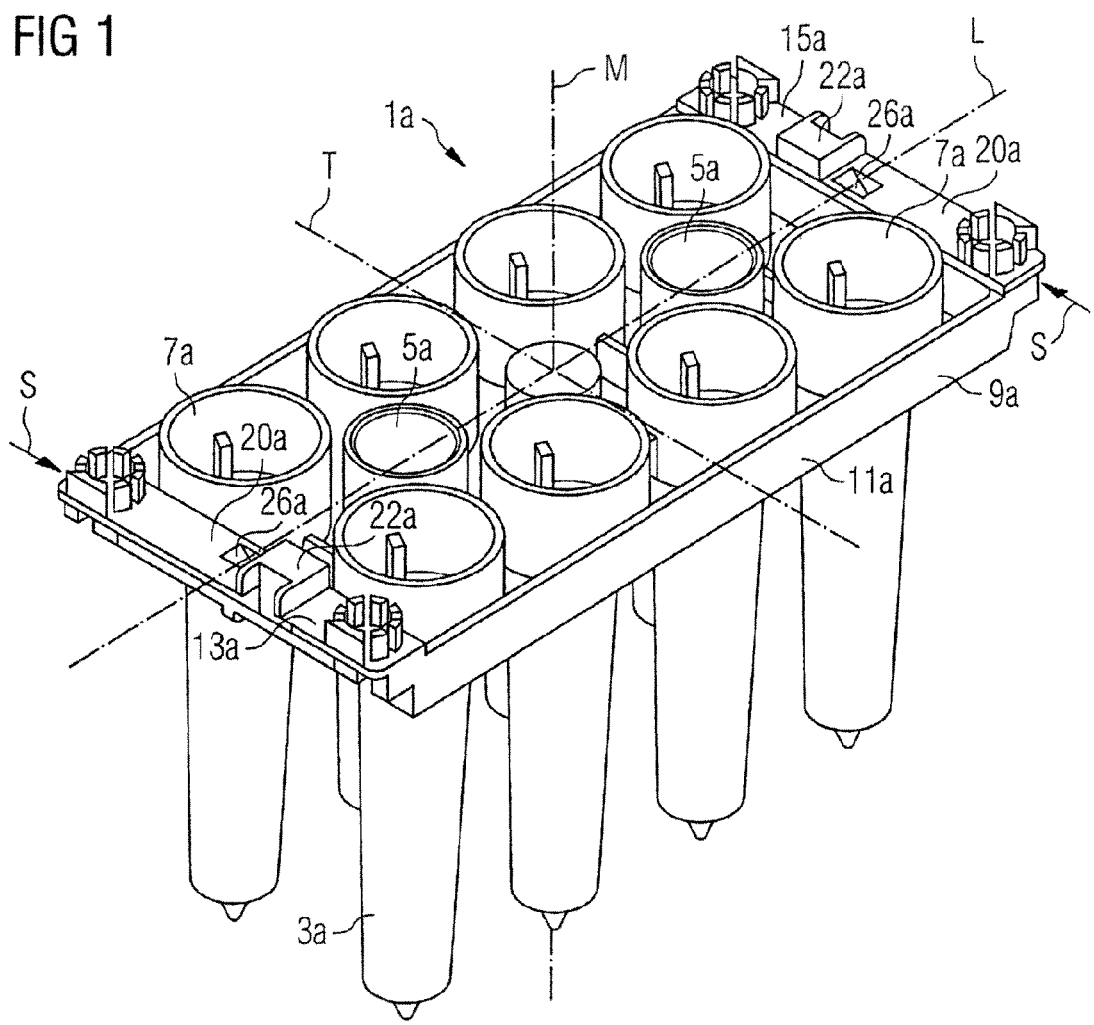

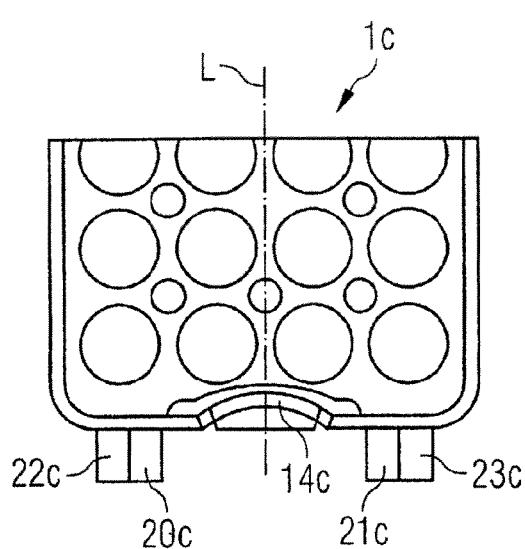
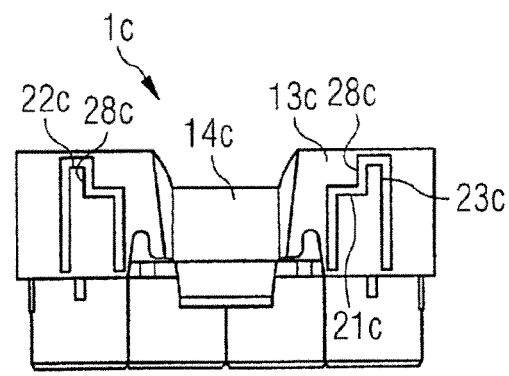
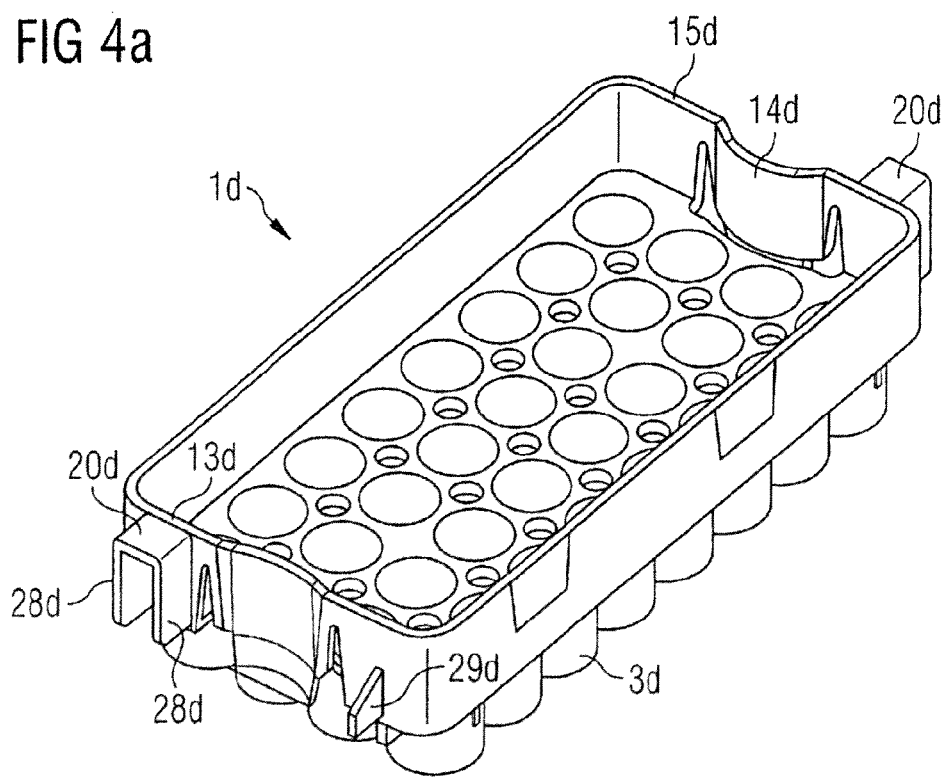

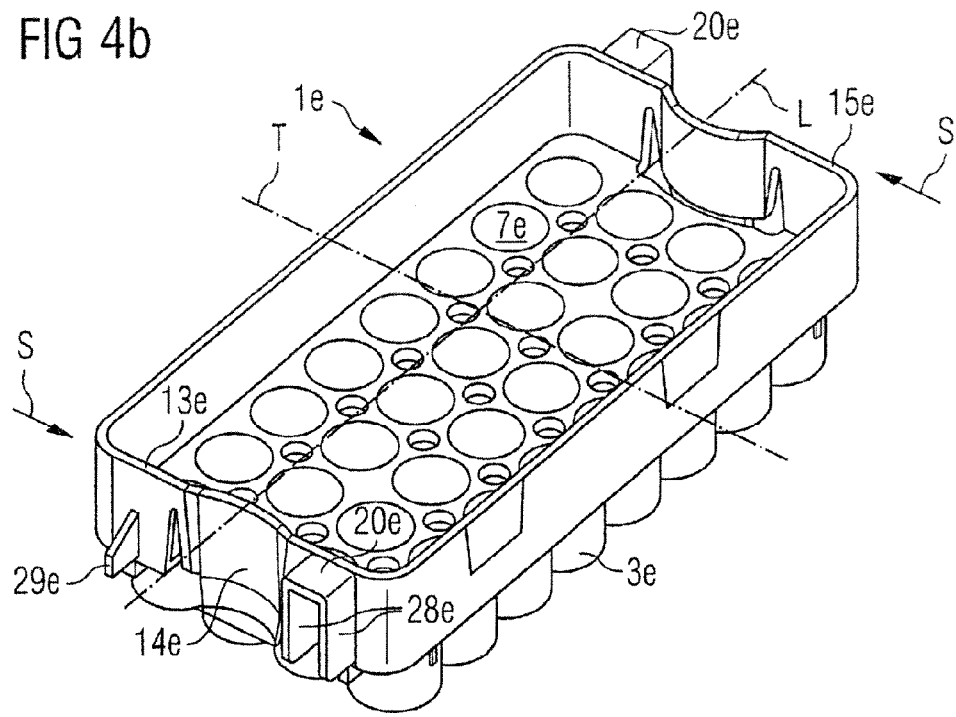
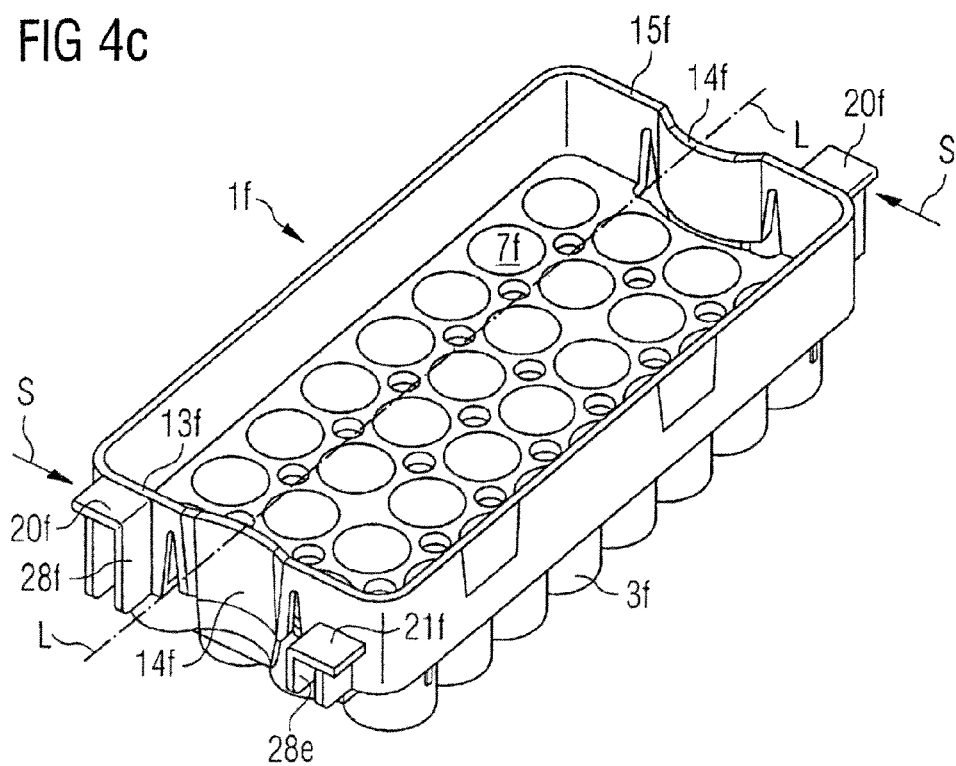

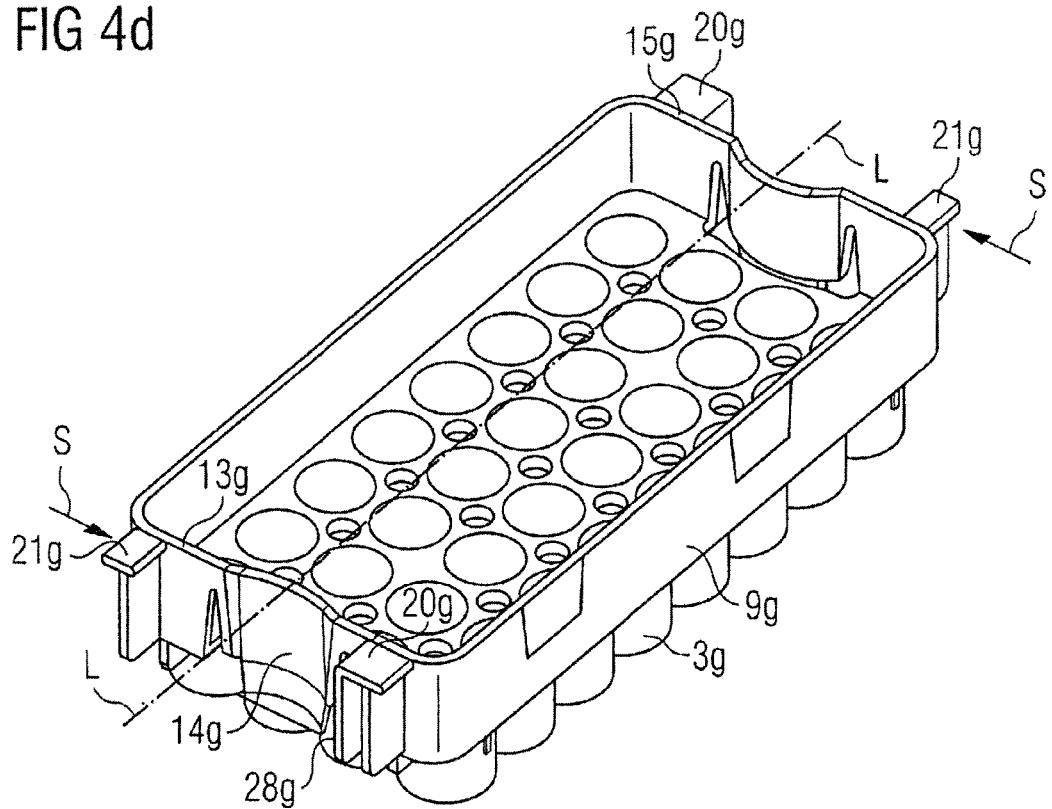

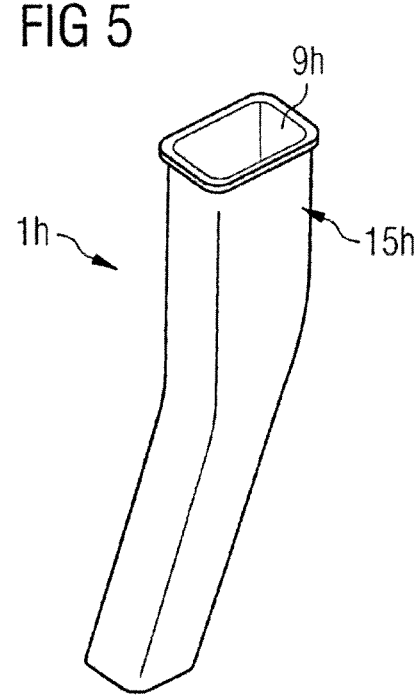
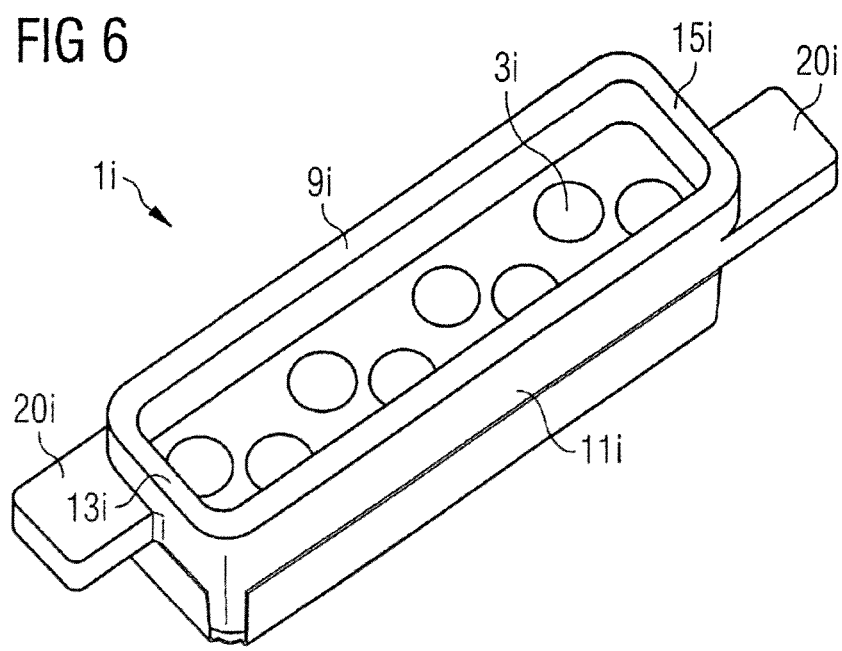

APPARATUS FOR PROCESSING BIOLOGICAL MATERIAL

CROSS REFERENCE TO RELATED APPLICATIONS

This application is a §371 National Stage Application of PCT/EP2008/060901 filed Aug. 20, 2008, which claims priority to European Application 07016283.9 filed Aug. 20, 2007.

BACKGROUND OF THE INVENTION

Field of the Invention

Embodiments of the present invention relate to an apparatus for the purification, respectively processing and/or analysis of biological target molecules, in particular to one with the detection device for detecting at least one object. Further embodiments of the invention relate to a receiving device for receiving material for processing, purification and/or analysis of biological target molecules, and a method for inventorying, for position determination and/or for arrangement determination of objects, in particular of receiving devices, which are used on a corresponding apparatus for automatic processing of a material, which includes biological target molecules.

Description of Related Art

Nowadays it is often desired, for isolating and further processing or analysing of biological target molecules such as nucleic acid and proteins, to use automated methods. This has many advantages, for example enabling a high throughput of samples, identical processing conditions at each isolation/process, which allow for a direct comparison of results of the process results, time saving, a reduced danger for employees to come into contact with substances potentially dangerous to health, which are often used in such processes, etc. To guarantee a smooth workflow of the process on the apparatus, it does not only have to be insured that the needed consumables and chemicals are located on the apparatus prior to initiation of the processes, but also that the right materials are located at the right position, in the right arrangement or alignment, in the right quantity and in the right state, for example opened.

With many devices on the market the user has to make sure that these conditions are fulfilled. That these conditions have not been fulfilled is often realized only when problems arise in the course of the processes, which can result in the lost of samples, time and consumables and, in the worst case, in a damaging of the apparatus.

With some devices on the market attempts are made to take away these tasks from the user and to conduct them automatically.

So far, it is known in the art to recognize process containers via an optical image recognition in a process room for biological material. An algorithm thereby tries to recognize contours of the process containers from a captured optical image and to determine the type of the process containers from the contours. This image recognition only works reliably if a sufficient optical contrast between the process container and a working table exists.

Further it is known to detect the presence of a disposable tip by picking up the disposable tip and measuring of a force for the process control. Thereby, a detection of the disposable tip is made in a rack for disposable tips at a first position. If this fails a next position is approached and the process is repeated until a correct detection of a disposable tip has happened. From this it is concluded that all further positions are filled, too. The detected disposable tip is subsequently thrown into a waste container. This process has to be repeated for each rack for disposable tips. The position of the disposable tip is permanently programmed in a software for the supervision of the process.

It is also known to determine the presence of process containers via a force measurement, preferably indirectly via the power consumption of the actuator of the gripper. Therein, a size and position of the process container is programmed in a software. The correct size and position can be determined by a fixedly defined sequence of gripping processes. This determination, however, is not sufficiently reliable precise and/ore fast under circumstances.

SUMMARY OF THE INVENTION

Therefore, it is an object to provide an apparatus for purification, processing and/or analysis of biological target molecules in such a way that the disadvantages of the prior art are overcome. In particular, it is desirable, to guarantee a save execution of processes on the apparatus, to inventory objects located on the apparatus such as receiving devices and consumables such as, e.g., process containers, disposable tips, storage containers, waste containers, containers for consumables etc., and to compare with the planed process and the consumables needed thereto. To exclude user errors this inventorying should take place automatically.

A further object consists in providing a corresponding method. Further, the process control is to be enhanced, for example via an enhanced supervision of parts belonging to the apparatus or being separately moveable, the detection of the presence and/or the position of objects located on the apparatus, in particular of drawers (position and arrangement or alignment) or of receiving devices.

This problem is solved by an apparatus for purification, processing and/or analysis of biological target molecules with a detection device for detecting at least one object, which includes at least one detection area, wherein the detection device is respectively adapted to detect at least one height value of the detection area and to determine, from the at least one height value, a spatial position and/or an arrangement/alignment and/or a type and/or a presence and/or a number and/or a state of the at least one object.

DETAILED DESCRIPTION OF A PREFERRED EMBODIMENT

Under the term height a difference to a reference height is generally understood, wherein the reference height can, e.g., be defined by the position of the detection device, but also, e.g., by a supporting surface of the object. Particularly, the height concerns a vertical distance. The height can also be defined as a distance in a direction which is orthogonal to a supporting surface of the object or, the case may be, as a distance in direction of a receiving opening of the object (for example a receiving device). Typically, a working plane is defined by the apparatus, and the height is then normally a distance in a direction orthogonal to this working plane. The reference height can also be understood as the height of the working plane or of the receiving device or of a part thereof.

For example, for determining the height with respect to a reference height, it is conceivable that the detection device knows its exact position such that the height value results from a simple distance measurement between the detection area and the detection device. It is also conceivable that the detection device conducts a measurement of its distance to the reference plane, for example to a working table, and subsequently determines the height of the detection area by forming the difference between the distance to the detection area and the distance to the reference plane. With the apparatus according to the invention it is possible, with only one detection device including a sensor, to detect parameter, which can be used for several purposes such as the determination of spatial position, of the arrangement/alignment, of the presence, of the state, of the number and/or of the type of the object. The term state for example means that the object on hand is opened or closed.

Although it is particularly advantages that generally the use of only one detection device is sufficient for determining the spatial position, the arrangement or alignment, the presence, the state, the number and/or the type of the object, it is also possible to use several detection devices in the apparatus, should this be desired. The properties of the detection device described in the following can completely or partially exist therein in only one detection device as well as in several detection devices.

In embodiments, the object to be detected is a receiving device. The receiving device can be, e.g., the tip of a pipette, in particular a disposable tip, or can be formed by a rack (holder for, e.g., tips of pipettes). A rack for tips of pipettes can for example have different geometrical features depending on the type, respectively size, of the tips of pipettes contained therein (e.g. number, width and height of rips and partitioning walls), wherein the features can be detected by the detection device such that the type, respectively size, can be recognized via these features. Further possible receiving devices are represented, for example, by process containers such as reaction tubes and/or storage containers, waste containers and/or supply containers for consumables, by covers for device parts to be protected and similar containers which are usually used in such automated applications.

The apparatus can further, for example for a moveable or slidable object such as a drawer, perform a check of the exact position of the object. For this, specific features of the objects are measured after its closure (e.g. cut-outs respectively recesses/gaps in the cover plate). These positions are compared with data stored in a configuration file such that deviations can be determined and be taken into consideration in the further process. This is of particular relevance in pipetting, e.g. in small containers, respectively small well geometries in multi well plates, or in an exact positioning of process containers, which are respectively received by the drawer, and it serves for enhancing the robustness of the process.

Recognition according to height values has the advantage as compared to an optical image that it allows for a certain independence of the colour-related and optical design of the objects. Therefore, the colour can be relatively freely chosen and, for example, be used for other purposes.

In a preferred embodiment, the detection device is adapted to determine the difference between the at least one detected height value of the object and a reference height value, and to determine a number of stacked objects from the difference. The detection device can, e.g., detect the height value of the object or the objects for this purpose, can determine a difference with respect to a reference height value, and can compute a number of stacked objects from the difference, respectively can assign the difference to a number of stacked objects. The apparatus can further be adapted to determine, from the at least one height value of the object, also the type of the stacked objects besides their number, namely for example by recognizing that the height value is a multiple of the stack height of one of the objects coming into question, but not of the other objects coming into question. Thereby, two information items of the object can be determined by a single measurement via an efficient use of the detection device. The term stack height is to be understood therein as the additional height by an additionally stacked object. While the stack height is the same for each object of the same type, it can be different for objects of different type.

In a further embodiment of the invention, the presence of an object can be determined from its at least one height value. These embodiments allow for carrying out inventorying of a working table in a process space by height-wise scanning of, e.g., the working table. The height values, respectively the three dimensional height profiles, which results there from, then suggests the consumables located on the device. Further, geometric features (e.g. edge positions and heights) can be detected for moveable objects or parts, and by comparing nominal parameters (e.g. a nominal position) with actual parameters (e.g. an actual position) of these features deviations can be determined and be taken into account while handling working materials respectively consumables.

A preferred embodiment of the invention is distinguished in that the detection device is adapted to detect at least one height value of an object with a one-point measurement. A one-point measurement means that a height measurement is carried out at a discrete point of the object (as the case may be, several times at the same, respectively a similar place, i.e. deviations, which result from, e.g. process precisions, respectively positioning these positions of the systems, are also subsumed therein), and this height measurement taken for itself is consulted for determining the number, the presence, the spatial position, the state and/or the type of the object. Particularly preferably, this height measurement is used for the common determination of several of these parameters.

A further preferred embodiment of the invention is distinguished in that the detection device is adapted to detect at least two height values, in particular a height profile arranged along a line, of at least one detection area of an object. The line can extend over one or several detection areas of the objects. In contrast to the one-point measurement a measurement of a height profile of an object includes the measurement of at least two different points, which are determined by two separate measurements of the detection device. Therein, the detection device can be transported to the at least two points, at which the measurement is carried out, (e.g. if the area to be measured is spatially fixed). Preferably, the detection device is arranged moveable relatively to the object. It is also possible to spatially fix the detection device and to move the area to be measured in particular along the line to be measured. The at least two different points can be spaced apart differently or equally from the detection device independently of one another, and, therefore, have a different or an identical height for the detection device.

In a preferred embodiment the apparatus is arranged to detect at least two height profiles. While measuring preferably at least two height profiles of an object, these lie preferably on opposing sides of the object, although it is also imaginable to detect a second or more height profiles for example as control or controls along the same line. It is further preferred that the two or more height profiles are detected respectively in directions opposed to each other. Therein, it is imaginable that the two height profiles detected in opposing directions are detected along the similar or the same line only in different directions or that the detection is carried out on different detection areas of the object.

Therein, a detection in opposing directions on two front sides of the object opposing each other is particularly preferred. By measuring two or more height profiles per object the certainty and precision of the measurement can be enhanced, and additional information can be detected, for example about a twisting of the object. In most cases measuring two height profiles is sufficient.

In a particularly preferred embodiment, the detection device includes at least one, preferably a exactly one, radiation source for eradiating the detection area, which can generate three-dimensional images, and/or at least one, preferably exactly one, sensor for measuring the intensity of the radiation, which emanates or comes from the detection area. A three-dimensional image in the sense of the invention means that a height value is detected respectively in dependence of position in a plane orthogonal to the height direction, wherein the position in the two dimensions of the plane orthogonal to the height direction is variable. Therein, parts (lines or single points) as well as the complete plane can be detected. The radiation emanating from the detection area preferably includes the radiation of the radiation source reflected by the detection area. The radiation source and the sensor are arranged in an angle relatively to each other, preferably in a substantially right angle, to the line, along which the height profile or the height profiles is measured or are measured. This allows for a height measurement for example by means of triangulation, with which only small dead angles in longitudinal direction have to be accepted because of the spatial displacement between the radiation source and the sensor.

In a preferred embodiment, the apparatus includes a processing space, wherein, preferably, the area detected by the detection device is arranged in the processing space, in particular is a predetermined area in the processing space. Therein, a predetermined are of the processing space is adapted to receive at least one object, wherein the predetermined area is, in particular, a receiving container or a drawer. In this way, not the whole processing space has to be scanned or detected to find an object, which is to be identified and/or which is to be received by the transporting device. An increased speed in inventorying the processing space is the result. In a preferred embodiment, the detection device is arranged moveable relatively to the object in the processing space. Thus, by scanning the processing space, inventorying is possible.

In a particularly preferred embodiment, the apparatus includes a transporting device for transporting the object. Therein, the detection device can be preferably arranged directly at the transporting device for transporting the at least one object, or, at least, in its vicinity. Thereby, only one moveable device would be necessary in the processing space, which leads to caused savings and to a control or regulation with smaller complexity. Such an arrangement has the advantage that not only the objects arranged in the processing space can be detected, but also that a process control can take place during a pick up, transporting, or releasing of the object. This enables the save handling of objects, that is, the reception, the transport and the release of the objects, and the control of consumables located on the transporting device. Thus, the whole process chain can be supervised: the position and type of the objects located in the processing space as well as on the process area, the position of the objects on the transporting device and the save release of the object or of the objects on the process area.

In a preferred embodiment, the at least one height value of the detection area of an object taken or received or picked up by the transporting device, in particular of an object most proximal or closest to the sensor of the detection device of a multitude of objects taken by the transporting device, preferably stacked objects, is detectable by the detection device. Hence, not only the type of the object, but also the number of the stacked objects is detectable, namely via the distance or separation between the object most proximal or closest to the sensor and a reference plane or a reference height. This method can also be applied to stacked objects arranged on the process table or arranged otherwise in the processing space, as long as the position of the reference plane is known to the detection device or to an evaluation unit belonging to the detection device. Further, the height of a single object must thereto be known to the detection device or to the evaluation unit after identifying the object via the height profile, or must be determinable by the detection device, to afterwards determine the number of objects by the distance, which includes the sum of the heights of the single stacked objects, and by the height of a single stacked object.

In a preferred embodiment, the sensor is implemented as a ultrasonic sensor or as a laser sensor. A combination of ultrasonic sensor and laser sensor in one or more parts is also possible. Such sensors are usually used in industry for distance measurement. Additionally, the detection device can have an ultrasonic emitter and/or a laser as radiation sources. In general, all radiation sources are suitable for the present invention, which are capable of determining a height and of generating three-dimensional images.

According to a further aspect of the invention, a receiving device for receiving material for processing, purification and/or analysis of biological target molecules is provided. The receiving device has at least one identification element, wherein the at least one identification element defines a height profile for the identification of the receiving device, wherein the height profile is provided for at least one height measurement and extends, at least in sections, along a line, preferably a straight line. Therein, the line can extend along an outer contour of the receiving device. By arranging the detection area along a line, the detection area of the object needs only be scanned along the line. The line can also be arranged in a curve or in a segment of a circle. As a height profile, a profile with at least two different heights is understood, wherein a height can also be detected as "infinite", in particular in existence of a faulty measurement, if the identification element has a gap such that the detection device detects, for example, the distance to the supporting surface of the receiving device or to a different object. The height profile serves for identifying the receiving device in order to distinguish one type of receiving device from another type of receiving device.

In a preferred embodiment the height profile can be provided for having at least one identification area for height measurement, preferably at least two identification areas for height measurement, wherein the identification areas have, independently of each other, the same or different heights. Hence, a multitude of receiving devices can be distinguished.

Therein it can preferably be intended that the at least two identification areas are adjacent to each other and/or are arranged with a distance from each other along the height profile, in particular along the line. Thus, in a preferred embodiment, the at least one identification area can have, in particular, a length along the line of substantially 1 mm to substantially 10 mm, preferably from substantially 2 to 8 mm, further preferably from substantially 3 to 6 mm. Also it can be provided that the height profile has at least two identification areas, which have a different length along the line.

Therein, in a preferred embodiment, the at least one identification area has a width of substantially 1 mm to substantially 10 mm transverse to the line, preferably from substantially 2 to 8 mm, further preferably from substantially 3 to 5 mm. It can also be designed that at least one, preferably each, of the at least one identification area is quadrangular, preferably rectangular. In general, also other forms of areas are imaginable as identification areas such as round, elliptical or multi angular identification areas, wherein these areas should then at least include the minimal quadrangular, respectively preferably rectangular base area.

In a preferred embodiment, the height profile has at least one detection edge, which respectively is adjacent to an identification area, and is formed preferably between the identification area and a respective connection area orthogonal to the identification area. Therein, the edge can be arranged substantially orthogonal to the longitudinal extension along the line, along which the height profile is detected. The at least one edge may be suitable for distinguishing the object from another object.

Hence, in a further preferred embodiment, two identification areas are adjacent to opposing sides of a connection area, wherein both identification areas being adjacent to the connection area have different heights and, optionally, different length and/or widths, wherein, in particular, the connection area is arranged along the line between both identification areas.

In a particularly preferred embodiment, the height profile is substantially symmetric, preferably mirror/reflection symmetric or point symmetric with respect to a mirror plane orthogonal to the line, which extends particularly along the outer contour of the receiving device. It is within the knowledge of the persons skilled in the art how the identification areas can be arranged relatively to the mirror plane to obtain, for example, a mirror symmetric or point symmetric height profile. Therewith, the certainty of a correct recognition of the receiving device can be further enhanced. Because of the preferred detection of the height profile along a line, which takes place in direction of the longitudinal extension of the identification area or the identification areas, the identification areas on both sides of a plane, which is substantially orthogonal to the line, along which the height profile is measured, can have a different width without changing the height profile.

It can also be designed that the height profile is not shaped symmetrically, preferably not mirror/reflection symmetrically or not point symmetrically.

Therein it can be provided that the identification areas on both sides of a plane, which is substantially orthogonal to the line, along which the height profile is detected, have a different length and/or height, and, optionally, additionally a different width.

In a preferred embodiment the receiving device has an outer contour with at least two opposing sides, wherein the opposing sides respectively include at least a first or a second identification element, which are, particularly, formed axially symmetrically with respect to each other to a middle axis of the receiving device. Hence, when a height profile is scanned on both sides by the detection device, a higher certainty at the recognition of the type of the receiving device can be obtained by the double scan or detection.

In a preferred embodiment, the receiving device has an upper side, from which the material to be received is extracted from or taken from the receiving device parallel to a middle axis, respectively is released into or disposed in the receiving device, wherein the height profile is arranged in such a way that a height measurement of the height profile may be realized from above. Therein, at least one of the identification areas, preferably all identification areas, can be arranged orthogonally to the middle axis.

It can be provided that at least one of the identification areas has substantially the same height as an upper edge of the receiving device.

In a preferred embodiment the material to be received by the receiving device is from a group including consumables such as a process container or a disposable tip; a device part to be protected from direct contact, such as, for example, a magnet for influencing the sample; a material for the processing, purification and/or analysis of the biological target molecules, such as, for example, a sample mixture or sample liquid with the target molecules, a lysis mixture, binding mixture, buffer mixture, washing mixture, elution mixture or other process mixtures such as enzymes, probes, pipetteable separating materials such as suspensions from magnetic beads, base materials for downstream applications such as PCR, assays and/or arrays.

In one embodiment, it can be provided that the receiving device has at least one receiving container closed at one end for receiving the materials. Therein, the receiving container can include a volume of from 8 µl to 7000 µl, preferably from 10 µl to 5000 µl, most preferably from 15 µl to 3000 µl.

In one embodiment, the receiving device has a plurality of receiving containers, preferably 8 receiving containers, wherein the receiving containers are preferably arranged in matrix arrangement.

In a further preferred embodiment, the receiving device has at least one receiving area open on two, preferably opposing, sides for receiving material. Examples for such a receiving device are disposable tips.

It can also be designed that the receiving device has at least one passage, preferably at least two passages, for passing through a lifting element of a transporting device, wherein the passage or the passages extends or extend parallel to the middle axis.

In a preferred embodiment, the receiving device is shaped in such a way that two receiving devices arranged one on top of the other are engaged in such a way that the receiving devices arranged on top of each other are stackable in predetermined alignments or orientations with respect to each other, and preferably have a common total height, which is less than the sum of the single heights of the receiving devices, wherein the receiving devices are preferably stackable in such a way that the respective passages of several stacked receiving devices are aligned along a line with respect to each other. Therein, the stackable receiving device can have a stack height of less than 80% of the total height of the receiving device, wherein the stack height preferably is less than substantially 50 mm and/or more than substantially 5 mm, further preferred between 10 and 40 mm and most preferred between 15 and 30 mm. Therein, the lower side of a receiving device can be put on the upper side of a receiving device for stacking. In embodiments, the receiving device is formed integrally in one piece, for example formed from one plastics part (preferably on polymer basis).

In one embodiment, it can be provided that a sidewall of the receiving device has a flexible pressure area to be pressed by a human finger, which extends in direction of the scanning line partially between two identification areas.

The object can be a receiving device for receiving containers, consumables, liquids and/or similar things. In particular, the object can be a process container, a disposable tip, a disposable cover or another consumable, or a rack for at least one process container, one disposable tip, one disposable cover or one other consumable, or can be a drawer or a waste channel.

According to a further aspect of the invention, an apparatus as described above is provided for an object as described above, preferably in form of a receiving device as described above.

According to a further aspect of the invention, a method is provided for inventorying, for position determination and/or for orientation determination of objects, which are needed for processing of a material, which includes biological target molecules, on a corresponding apparatus, in which method at least one height value of a detection area of the respective object, such as a drawer, a container, consumables and/or similar things, are detected; and in which, from the height value, a spatial position and/or an orientation/alignment and/or a type and/or the presence and/or the number and/or the state of the respective object on the apparatus is determined.

The objects can concern components of the apparatus, for which the determination of the spatial position, of the orientation, of the type and/or of the state is important for the process course, or can concern objects disposed on the device, wherein for the latter also the presence and/or the number can be relevant additionally to the other aspects named above. Examples for such components of the apparatus are drawers, waste containers for consumables and chemicals, adapters for the reception of primary or secondary reaction tubes, respectively sample containers, adapters for the putting down of used disposable tips for later reuse. Examples for objects put on the device are represented by the once named above.

In a preferred variant of the method, a one-point measurement for detecting the height value is executed for determining the spatial position and/or the type and/or the presence and/or the number and/or the state of the object. The value thereby obtained is compared to correspondingly previously determined data. The result of the comparison is then used for control of the workflow of the process on the apparatus. If deviations between the result obtained at the measurement of the height value and the previously determined data occurs, an indication can, preferably optionally, be provided. In such a case, the user could, if needed, change the parameter to remove the deviation. Thus, problems in the course of the processes could be avoided, e.g. by consumables not sufficiently provided for the planned process, nor by closed containers, incorrectly loaded consumables, a displacement of the position of the objects by errors during loading, and a smooth process course could be guaranteed.

A further preferred embodiment is distinguished in that at least two height values, in particular a height profile, of the detection area are detected, wherein, preferably, the height profile is arranged along a line. Therein, the at least one height value, in particular, the height profile, can be an identification pattern, from which the type of the object is determined. The obtained height values, in particular the height profile, are compared with corresponding previously determined data, and the result of the comparison is used for control of the course of the process on the apparatus. If deviations between the result obtained at the measurement of the height values, in particular the obtained height profile, and the previously determined data occur, an indication can be provided, preferably optionally.

In an embodiment, at least one calibration height profile along at least one calibration line is detected prior to the detection of the first height profile. Further, it is possible, if desired, to determine a calibration height profile during the course of the process, even if this will not be needed in most cases. Moreover, several calibration height profiles can be detected along the same calibration line. Therefrom, averages can for example then be formed. Also, several height profiles can be detected along several calibration lines to be able to determine, respectively exclude, potential deviations or errors. As the effort increases with increasing number of measurements, preferably less than 5 measurements are carried out along the same calibration line for calibration, further preferably less than 3 and even further preferably only 1. In a particularly preferred embodiment, the calibration height profile of at least one calibration line is measured, which is located at a position within the device, at which no objects are to be detected, and the subsequent height measurements use the obtained height profile as basis or reference profile. This means that the measured height profile is measured using information of the reference profile (such as the choice of the detection area in dependence of the reference profile) or is further processed (for example forming the difference between the height profile and the reference profile or an averaged or smoothened reference profile). Particularly advantageously, such calibration lines are located on the working area, for example in the area of the drawers.

In a further preferred embodiment, at least one height profile is measured along at least one calibration line, which extends, within the device, orthogonally to a first edge with a defined nominal position. Additionally, at least one height profile is measured along at least one calibration line, which extends, within the device, orthogonally to a second edge with defined nominal position, wherein the first edge is arranged perpendicularly to the second edge. From the obtained height lines of the previous measurements, the actual positions of the defined edges are determined. The actual positions of the edges are compared with their nominal positions and the information from the comparison between the actual positions and the nominal positions of the defined edges is used for control of the further course of process on the apparatus.

The first and/or second edge can therein be formed by the border of a quadrangular, preferably rectangular, recess or gap or protrusion.

Deviations can be determined with respect to the values stored in the system of the apparatus by the above measurements, which deliver so-called offset values. The determined discrepancies between the nominal values and the actual values can lead to different reactions. For example, the possibility exists to use the real actual position thereby determined in the course of the process for the definition of the position of other components or consumables of the apparatus, such as, for example, racks for pipette tips or multi-well plates with very small cross section, single sample containers, respectively reaction tubes, with small diameter. Cases can arise, in which the deviations are so dramatic that it does not make sense to adjust the subsequent process to such deviations. This is for example the case, if the nominal position of an open drawer is determined and this position deviates considerably from the actual position of the closed drawer. In such cases, in particular, it is therefore possible, for example, to display an error message if the discrepancy between the nominal positions and the actual positions of the defined edges surpass a previously determined value.

In a preferred embodiment, a respective height profile is detected several times along lines parallel to each other. The lines are respectively laterally displaced with respect to each other, preferably by less than 2 mm.

In a preferred embodiment of the method according to the invention, a number of stacked objects is determined from a height difference between the detection area of the object and a reference height. Preferably, several information items can be determined at the same time, namely, for example, the type and the number of the objects, from a measurement of the height value of the detection area.

In a preferred embodiment, the type and the number of the stacked objects is determined by the following formula:

$$h_T = (n-1) \times h_{SO} + d,$$

wherein $h_T$ is the height difference between the at least one detected height value of the detection area of an object with a determined height profile and a reference height, n (n>=1) is the number of stacked objects, $h_{SO}$ is a stack height between two neighbouring stacked objects, and d is a height of the detection area of the object (relatively to the defined reference point). The stack height $h_{SO}$ represents preferably the distance between the detection areas of two neighbouring stacked objects. Usually, this value is the same for a particular type of object, independently of how many such objects are stacked. The stack heights of different alternatives of an object may indeed be the same, however, they are preferably different (for example for different racks for pipette tips or different types of reaction tubes or storage containers). Objects being different by type can also have the same or different stack heights. Thus, for example, a respective rack for pipette tips and a type of storage containers can have identical stack heights, which, however, are different from the stack heights of racks for other pipette tips and a different type of reaction tubes, wherein the latter can, among each other, have the same stack height again. If there is only one object at the position, at which the measurement takes place, then n=1 and therefore $h_T$=d. If the height $h_T$ can be determined with sufficient precision and the stack height $h_{SO}$ or the detection height of the objects coming into question differ in suitable way, then the type of the objects as well as the number n can be deduced from the measured value $h_T$ in an unambiguous way.

Therein, at least one object can be taken by the transporting device, for example a grip, a spreader or the like, and the at least one height value of the detection area of the received object can be detected. Hence, preferably, the number and/or type of stacked objects is determined while the objects are located on or in the transporting device. It is further preferred that the height difference is determined based on the stacked object which is closest to the detection device and in particular to the laser and/or the ultrasonic emitter.

In a preferred embodiment of the method according to the invention, a number and/or type of stacked objects is determined while these are taken by the transporting device. Therein, it can be provided that, preferably, one or more of the taken and detected objects are deposed by the transporting device, wherein, preferably, single objects as well as several objects or all objects can be deposed simultaneously.

Preferably, it can be determined after the deposition whether the number of objects taken by the transporting device has decreased and/or whether the object has been released from the transporting device.

In a further preferred embodiment, the method according to the invention is distinguished in that the object has an area with several openings for receiving pipette tips, which preferably have a flange, which is larger than the openings. A height profile of the area can be detected or, in particular, at least one height value of a point on the border of respectively one of the openings, wherein the presence and/or number of pipette tips is detected via the height profile and/or the respective at least one height value.

By scanning the area within an object fillable with substances or several parts (respectively a receiving device), for example of a rack, i.e., within the frame of an object, the number of filled parts, for example of pipette tips or the presence of substances can be determined, because different geometric features occur at the same position of the fillable object, for example the racks, in presence of a filled part, for example a pipette tip, respectively a substance, as compared to empty receiving areas, respectively receiving containers of an object, for example of a rack. In this way, for example, the exact number of pipette tips and their position can be determined, no required position by a software programming is necessary such that user errors by wrongly positioned objects for the reception of disposable tips is excluded. Further, in contrast to what is described in the state of the art, no pipette tips are therein wasted because they are measured without contact.

After inventorying of a process area, such as a working table, a feedback can be given to the user at once about the number of possible processable samples with the chosen script or he can be asked for actions for example, to empty the waste container, to close drawers or to exchange incorrectly loaded consumables.

With the device according to the invention it can be checked also for containers or objects with covers, whether the containers are opened or are closed with a cover.

In case of an erroneous operation (cover closed), the user can, for example, be tasked with the opening. Additionally, parts and geometries in the processing space are always afflicted with certain tolerances. To target small containers or objects during processing in spite of this, the actual position relative to the robot or to the transporting device, can be measured with the method described above and be taken into account for the subsequent processing method.

The invention also refers to a device for carrying out the disclosed methods and includes also device parts for carrying out respective single method steps. The particular features described in connection with the method are, therefore, analogously transferable also to the device and the device parts. The method steps can be carried out by hardware components, by a computer programmed by means of corresponding software, by a combination of both, or in any other way. The invention is furthermore directed to methods, according to which the respective described devices work.

It includes method steps for carrying out each function of the devices. The particular features described in connection with the device or the device parts are, therefore, analogously transferable to the method.

Further features and advantages of the invention are evident from the following description, in which several embodiments of the invention are explained in detail with the help of schematic drawings.

FIG. 1 shows an object (receiving device) in a perspective view according to a first embodiment of the invention;

FIG. 3a shows a view from above of an object (receiving device) according to a third embodiment of the invention;

FIG. 3b shows a lateral view of the object according to the third embodiment of the invention from FIG. 3a;

FIG. 4a shows a perspective view of an object (receiving device) according to a fourth embodiment of the invention;

FIG. 4b shows a perspective view of an object (receiving device) according to a fifth embodiment of the invention;

FIG. 4c shows a perspective view of an object (receiving device) according to a sixth embodiment of the invention;

FIG. 4d shows a perspective view of an object (receiving device) according to a seventh embodiment of the invention;

FIG. 5 shows a perspective view of an object according to an eighth embodiment of the invention;

FIG. 6 shows a perspective view of an object (receiving device) according to a ninth embodiment of the invention;

Figure 2A:
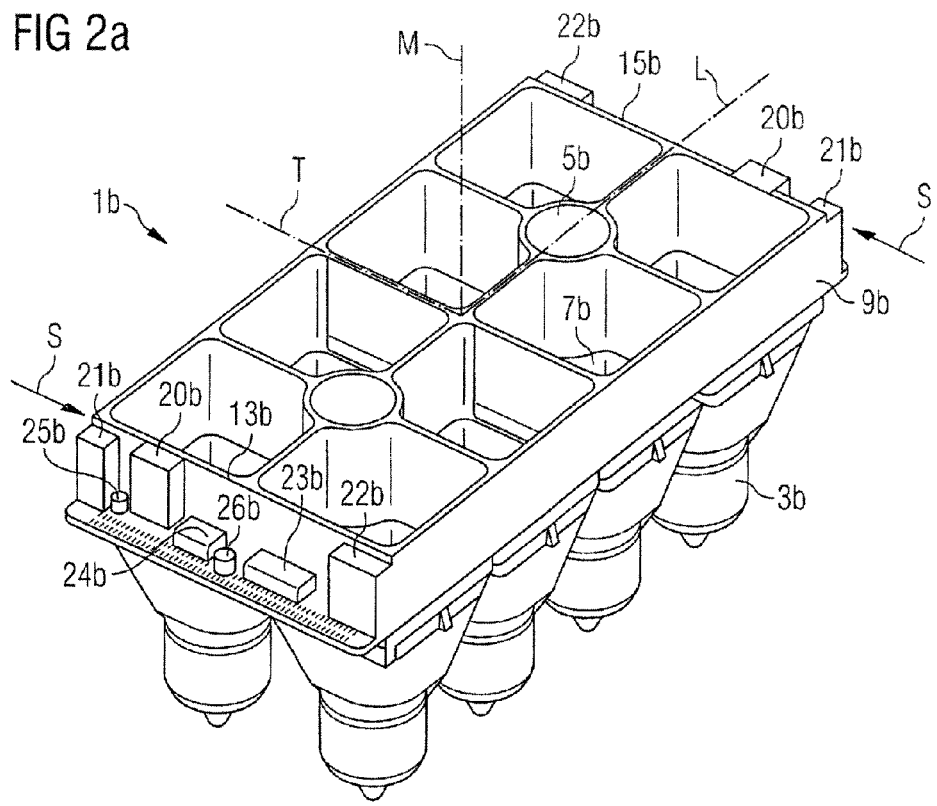
FIG. 2a shows an object (receiving device) in a perspective view according to a second embodiment of the invention.

FIG. 1 shows a first object according to the invention (receiving device) 1a. The first object 1a is a plastics part relevant for a process, which is transportable in a device (not shown) for purification or processing and/or analysis of biological target molecules. The first object 1a has eight receiving areas 3a into which, for example, a magnet can be inserted.

The first object 1a has two passages 5a. The passages 5a serve for the pick up of the first object 1a by a transporting device with two fingers, which are passed through the passages 5a (see FIG. 8 below).

The object defines a longitudinal axis L, a middle axis M, and a transversal axis T, which are orthogonal to each other. The object, and in particular the passages 5a, are nearly axially symmetric around the middle axis M, and (with the exception of the detection areas, see below) mirror symmetric to the planes L-M and T-M.

The receiving containers 3a respectively have an opening 7a at their upper end, the upper border of which is formed at the same height as the upper border of the passages 5a. "Up" is, for objects according to the invention, the side, in which the content of the receiving containers 3a can be disposed or from which it can be extracted. Around the openings 7a of the eight receiving containers 3a, the object has a rectangular frame 9a with two longitudinal sides 11a parallel to the longitudinal axis L and with two transversal sides 13a, 15a parallel to the transversal axis T.

At the transversal sides 13a, 15a, a respective recognition area or a detection area, is arranged. The detection area has an area 20a provided for a one-point measurement on one side with a predetermined height with respect to a reference height. The reference height can be defined by the supporting surface or the supporting edge of the object (for example, the lower or upper edge of the frame 9a). The height is determined by a measurement of the distance between the detection device and the detection area. At a one-point measurement, the relative position to the reference height is known to the detection device, such that the height can be determined as the (vertical) distance between the area designed for the one-point measurement and the reference height. From this height, the type of the object can then be recognized.

The detection areas, which extend respectively along opposing transversal sides 13a, 15a, additionally defined each a height profile running parallel to the transversal axis T. The respective detection area includes a projection with a detection area 22a, the area 20a designed for the one-point measurement, and a recess or gap 26a and two ridges at the outer edges of the projection with the detection area 22a.

The projection with the detection area 22a, the recess or gap 26a and the ridges each form edges in the height profile, the height and position of which along the transversal axis T can be read out relatively easily and reliably as identification feature, and, hence, are particularly suited for the identification of the objects.

When detecting the object by scanning of the height profile along a line along the transversal sides 13a, 15a (parallel to the transversal axis T), a measurement of the height is sufficient as a, preferably vertically, distance between the detection device (the position of which is defined relatively to a reference height) and the corresponding surface area part of the detection area. In this case, the identification of the object is possible by detecting and evaluating the edges of the height profile, as they are generated by sections of the detection area with different heights and can be recognized by the detection device.

The detection areas on the first and second transversal side 13a, 15a are arranged axially symmetrically around the middle axis M. Therefore, in both detection areas, similar or even identical height profiles are obtained if the height profiles are scanned in respectively opposite direction S. This allows for arranging the object in an obituary mirrored way without having an influence on the height measurement. Also, this allows for a measurement by scanning the detection areas of both transversal sides 13a, 15a, whereby the positioning of the objects can be recognized even more precisely.

Different objects can further be identified by different heights of the area 20a designed for the one-point measurement or by a different height profile along the transversal sides 13a, 15a.

In FIG. 2a a second object 1b according to the invention is shown. For the second object 1b according to the invention, areas with the same function have the same reference numbers as the first object 1a according to the invention, only with a "b" following the number instead of an "a". The second object 1b according to the invention concerns a plastics part relevant for the process as in the case of the first object according to the invention, more precisely stated a sample receiving container.

In the second object 1b, parts of the frame 9b also form the frame of the respective openings 7b at the same time. As in the first object 1a, the second object 1b has a detection area along its transversal sides 13b, 15b with an area or projection designated for a one-point measurement with a detection area 20b and a height profile for a multi-point or line measurement, which has edges (defined by projections with detection areas 20b, 21b, 22b, 23b, 24b, 25b with different heights). In the middle of the transversal sides 13b, 15b, a rectangular recess/gap 26b is formed. Thus, a detection device measures, if it detects the left detection area in scanning direction S in the scope of a line measurement, approximately the following height profile: high area, low area, high area, low area, recess/gap, low area, high area. Therein, the respective areas (defined by projections with the detection areas 20b, 21b, 22b, 23b, 24b, 25b) can have different lengths along the transversal sides 13b, 15b of the second object. By the arrangement and type of edges, which result from different lengths along the transversal side and from different heights of the detection areas of the projections or the recess/gap, the type of the object can be identified.

Figure 2B:
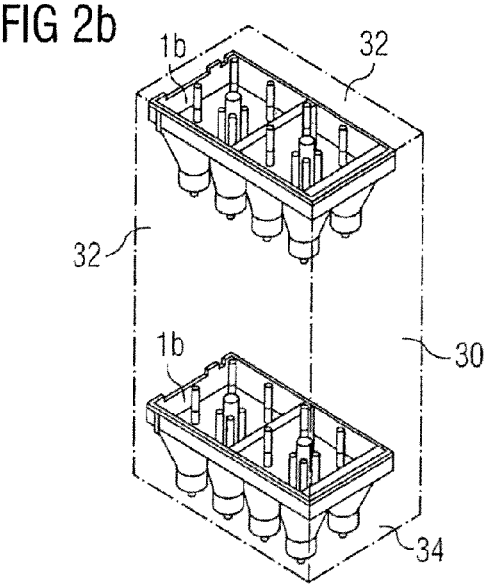
FIG. 2b shows a perspective view of the object from FIG. 2a of the second embodiment in a receiving container.

FIG. 2b shows a receiving container 30 in particular for the objects 1a and 1b according to the invention, wherein only objects 1b can be seen in the receiving container in FIG. 2b. The receiving container 30 is a packing unit in particular for the supply containers 1a or 1b and is insertable or pluggable in a device for processing of biological material, for example in a drawer thereof shown in FIG. 7. The receiving container 30 has two partial areas 32, which can respectively receive one or more stacked objects. Hence, the left partial area in FIG. 2 shows the lowest and upper most object from stack, wherein the objects lying in between are not displayed. A transporting device (see FIG. 8) can take out one or more objects at the same time from the receiving container 30 or can put therein.

FIGS. 3a and 3b show a third, FIG. 4a a fourth, FIG. 4b a fifth, FIG. 4c a sixth and FIG. 4d a seventh object 1c, 1d, 1e, 1f, 1g according to the invention. In the third, fourth, fifth, sixth and seventh object 1c, 1d, 1e, 1f, 1g according to the invention, areas with the same function have the same reference numbers as the first object 1a according to the invention, only with a "c", "d", "e", "f" or "g" following the number instead of an "a". The objects of the FIGS. 3a to 4d are formed identically or similarly with the exception of the identification elements.

The third object 1c of FIG. 3a has, on its transversal side 13c, a detection area for a line measurement, which includes two projections arranged symmetrically, preferably mirror symmetrically to the symmetry line in longitudinal direction L, which each have a first identification area 20c, 21c, and a second identification area 22c, 23c, wherein the second identification areas have a different height as the first identification areas and, preferably, the first identification areas are higher than the second identification areas. The first identification areas 20c, 21c are directly adjacent to the second identification areas 22c, 23c. Between the first identification areas 20c, 21c and the second identification areas 22c, 23c, there is arranged a respective connection area 28c, which connects the first identification areas 20c, 21c with the second identification areas 22c, 23c, such that an edge is formed between the connection area 28c (nothing is aligned using this area) and the identification areas. On the transversal side 13c, a flexible pressure area 14c is further arranged for pressing by the human finger. For better reachability of the pressure area 14c a gap is located in its vicinity between the identification areas 20c and 21c, which is adapted to the requirement of reachability.

The first identification area 20c/22c is therein arranged preferably on a side of a plane substantially halving the surface, in which the longitudinal axis L lies, while the second identification area 21c/23c is arranged on the other side of this plane. The identification area 20c/22c on the transversal side 13c is preferably arranged rotationally symmetrically to the identification area 20c/22c on the transversal side 15c (not shown), such that the face view of both transversal sides 13c and 15c are the same at least with respect to the position of these identification areas. An analogue applies for the identification area 21c/23c.

In a further embodiment (without figure), the first identification area 20c/21c can be combined with the projection 29c or can be combined with an identification area 22c or 23c having only one area, wherein their length can, optionally, be different from the one of the areas 20c or 21c.

The fourth object 1d according to the invention, which is shown in FIG. 4a, has each a projection with an identification area 20d on the transversal sides 13d, 15d. On both sides of the identification area 20d, the projection has connection areas 28d arranged perpendicularly or orthogonally to the identification area 20d, which each have an edge in common with the identification area 20d. Further, the fourth object according to the invention can have a further projection 29d, which serves for disposing the fourth object 1d. It can be dimensioned in a way that it is not detected by a detection device, which detects the height profile along the transversal sides. Thus, the type of the object can, for example, be detected by a line measurement of the height profile along a transversal side of an object, so that an object can be distinguished from another object (for example the third object 1c from the fourth object 1d).

The identification area 20d is arranged therein preferably on one side of a plane substantially halving the surface, in which the longitudinal axis L lies, while the projection 29d is arranged on the other side of this plane. The identification area 20d is arranged on the transversal side 13d preferably rotationally symmetrically to the identification area 20d on the transversal side 15d, such that the face views of both transversal sides 13d and 15d are the same at least with respect to the position of these identification areas. An analogue applies for the projection 29d.

In FIG. 4b the fifth object according to the invention is shown. It has, just like the fourth object 1d, each one projection with a detection area 20e and two connection areas 28e. Just as the fourth object 1d, the fifth object 1e has a projection 29e for disposing the fifth object 1e. The identification area 20e of the fifth object 1e is arranged mirror-invertedly to a longitudinal axis L just as the identification area 20d of the fourth object. Hence, the fourth and fifth object 1d, 1e can be recognized in a simple way (i.e., can be distinguished from objects of a different type and from each other).

The identification area 20e is therein arranged preferably on a side of a plane substantially halving the surface, in which the longitudinal axis L lies, while the projection 29e is arranged on the other side of this plane. The identification area 20e on the transversal side 13e is preferably arranged rotationally symmetrically to the identification area 20e on the transversal side 15e, such that the front views of both transversal sides 13e and 15e are the same at least with respect to the position of these identification areas. An analogue applies for the projection 29e.

In FIG. 4c the sixth object if according to the invention is shown. It has, on its transversal sides 13f, 15f, each two projections with a first identification area 20f or a second identification area 21f. The two identification areas have different heights, wherein the first identification area 20f is preferably higher than the second identification area 21f, and the first identification area 20f is arranged on one side of the symmetry line in longitudinal direction L and the second identification area 21f is arranged on the other side of the symmetry line in longitudinal direction L. In direction of the symmetry line in longitudinal direction, the projections have, adjacent to the identification areas 20f, 21f, each a connecting area 28f, which has an edge in common with the identification areas.

The identification area 20f is therein arranged preferably on a side of a plane substantially halving the surface, in which the longitudinal axis L lies, while the identification area 21f is arranged on the other side of this plane. The identification area 20f on the transversal side 13f is preferably arranged rotationally symmetrically to the identification area 20f on the transversal side 15f, such that the front views of both transversal sides 13f and 15f are the same at least with respect to the position of these identification areas. The analogue applies to the identification area 21f. The identification area 20f is preferably arranged higher than the identification area 21f.

In FIG. 4d, the seventh object 1g according to the invention is shown. It has, on its transversal sides 13g, 15g, each two projections with a first identification area 20g or a second identification area 21g. The first identification area 20g is, in scanning direction S, longer than the second identification area 21g, and the first identification area 20g is arranged on one side of the symmetry line in longitudinal direction L, and the second identification area 21g is arranged on the other side of the symmetry line in longitudinal direction L. In direction of the symmetry line in longitudinal direction, the projections have, adjacent to the first identification area 20g, a connecting area 28g, which respectively has an edge in common with the identification areas. The two identification areas 20g, 21g are arranged approximately at the same height as an upper border of a frame 9g of the seventh object 1g. In this case, the sizes or lengths, in scanning direction serve for the recognition of the seventh object.

The identification area 20g is therein arranged preferably on one side of a plane substantially halving the surface, in which the longitudinal axis L lies, while the identification area 21g is arranged on the other side of this plane. The identification area 20g on the transversal side 13g is preferably arranged rotationally symmetrically to the identification area 20g on the transversal side 15g, such that the front views of both transversal sides 13g and 15g are the same at least with respect to the position of these identification areas. The analogue applies for the identification area 21g. The identification area 20g preferably has a larger length than the identification of 21g.

The objects from the FIGS. 3a/b and 4a, 4b, 4c, 4d show receiving containers for pipette tips. As the height profiles vary independently of the size and type of the pipette tips, the size and type of the pipette tips located in the object can be identified from the height profile.

In FIG. 5, an eighth object 1h is shown. It concerns a waste channel for consumables such as disposable tips or chemicals. The waste channel 1h has a flange-shaped border 9h at its upper end 15h. The flange-shaped border 9h serves as stopper at a putting through of the waste channel 1h in an opening provided for the waste channel 1h in a drawer or a working table, such that the flange-shaped border 9h of the waste channel 1h rests directly on the border of the opening. The waste channel 1h is identifiable by the outer dimensions, in particular by the width of the flange-shaped border 9h. In this way, the presence or absence of the waste channel can be determined with a 1-point measurement by measuring the height in the area on a working plate, a drawer or the like, in which the flange-shaped border 9h should rest on the drawer or the working table. The height depends on the waste channel 1h being in its allotted place or not and can, therefore, be used for the retrieval of this information.

In FIG. 6, a ninth object 1i in accordance with the invention is shown in form of a holder for disposable tips. Areas with the same functions have the same reference signs as the first object 1a in accordance with the invention, only with an "f" following the number instead of an "a". The holder of disposable tips 1i can be removed for cleaning from a process space or from a process table or from a drawer, an has several receiving areas 3i for receiving disposable tips. To determine whether the holder for disposable tips 1i is arranged at its place in the process space or on the process table, it has at its transversal sides 13i, 15i a detection and calibration protrusion 20i as detection area. By means of a 1-point measurement as in the case of the waste channel, the presence of the holder of disposable tips can be determined. By detecting the height profile at both transversal sides 13i, 15i, it can be additionally determined whether the holder for disposable tips was arranged correctly at its place, i.e., whether it is, e.g., not tilted/jammed.

Figure 7:
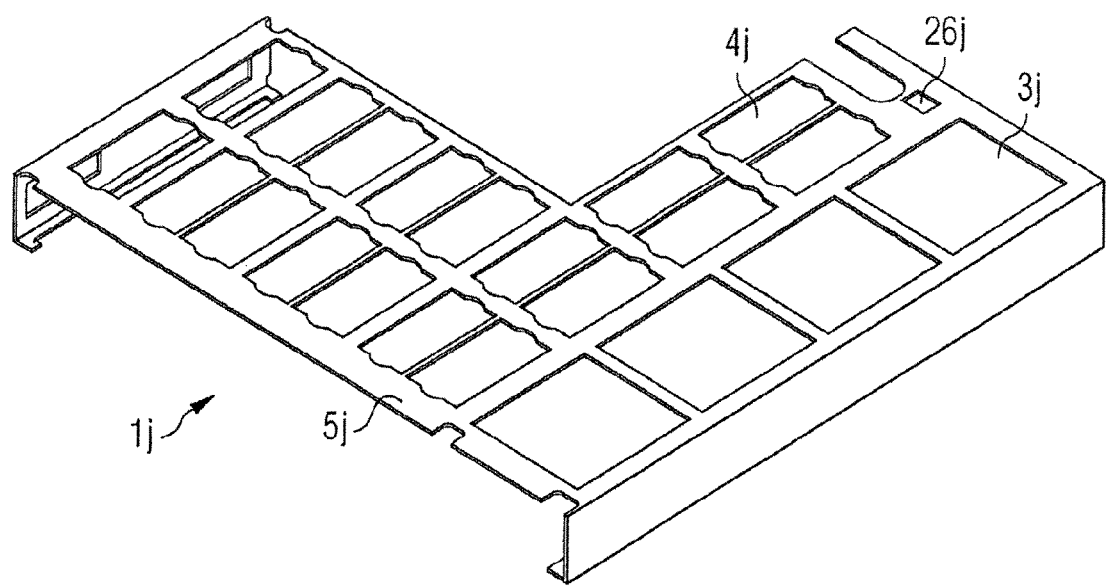
FIG. 7 shows a perspective view of an object (receiving device) according to a tenth embodiment of the invention.

FIG. 7 shows a tenth object 1j according to the invention in form of an upper part of a drawer. The upper part of the drawer 1j has a multitude of receiving openings 3j, 4j, which are dimensioned in different sizes. In this way, for example, a waste channel according to FIG. 5, a first, second, third, fourth, sixth, seventh or eighth object of a receiving container 30 can be arranged in one of the receiving openings 3j or 4j. Additionally, a surface 5j of the upper part of the drawer 1j has a detection area at a border area of the upper part of the drawer 1j with a quadrangular, preferably rectangular, recess or gap 26j. From an exact position of the recess 26j or from the positions of the borders of the preferably rectangular recess 26j, the position of the drawer 1g can be determined. Measuring the position of further recesses or gaps can allow for an enhanced determination of the position and/or of the orientation of the drawer 1j. The identification of further objects, which are placed in or on the drawer, can take place in dependence of the position and/or orientation measurement of the drawer. For example, the position, at which a line or 1-point measurement is to be conducted, e.g. for identifying such an object, can be chosen dependent on the result of the position and/or orientation measurement of the drawer.

The detection device preferably includes a laser scanner with a laser emitter and a photo diode cell arranged displaced thereto. Such a laser scanner is obtainable, e.g., from the Baumer company (Model No. OADM 1316480/S35A or OADM 1316475/S35A).

For distance measurement with such a laser scanner, triangulation can be used. In the triangulation method, a laser ray is directed substantially perpendicularly on the object to be scanned. The point appearing there is projected onto the photo diode cell via an optical system. The distance of the object is then computed by means of the incidence angle (position of the point mapped onto the photo diode cell).

Alternatively, the detection device can realize distance measurement by other devices, too. Thus, an alternative embodiment of the detection device can be based, likewise, on a device for laser run-time/delay time measurement or for laser interference measurement or for ultrasonic measurement (with ultrasonic sensor and emitter), or on any combination of several of such devices.

Figure 8:
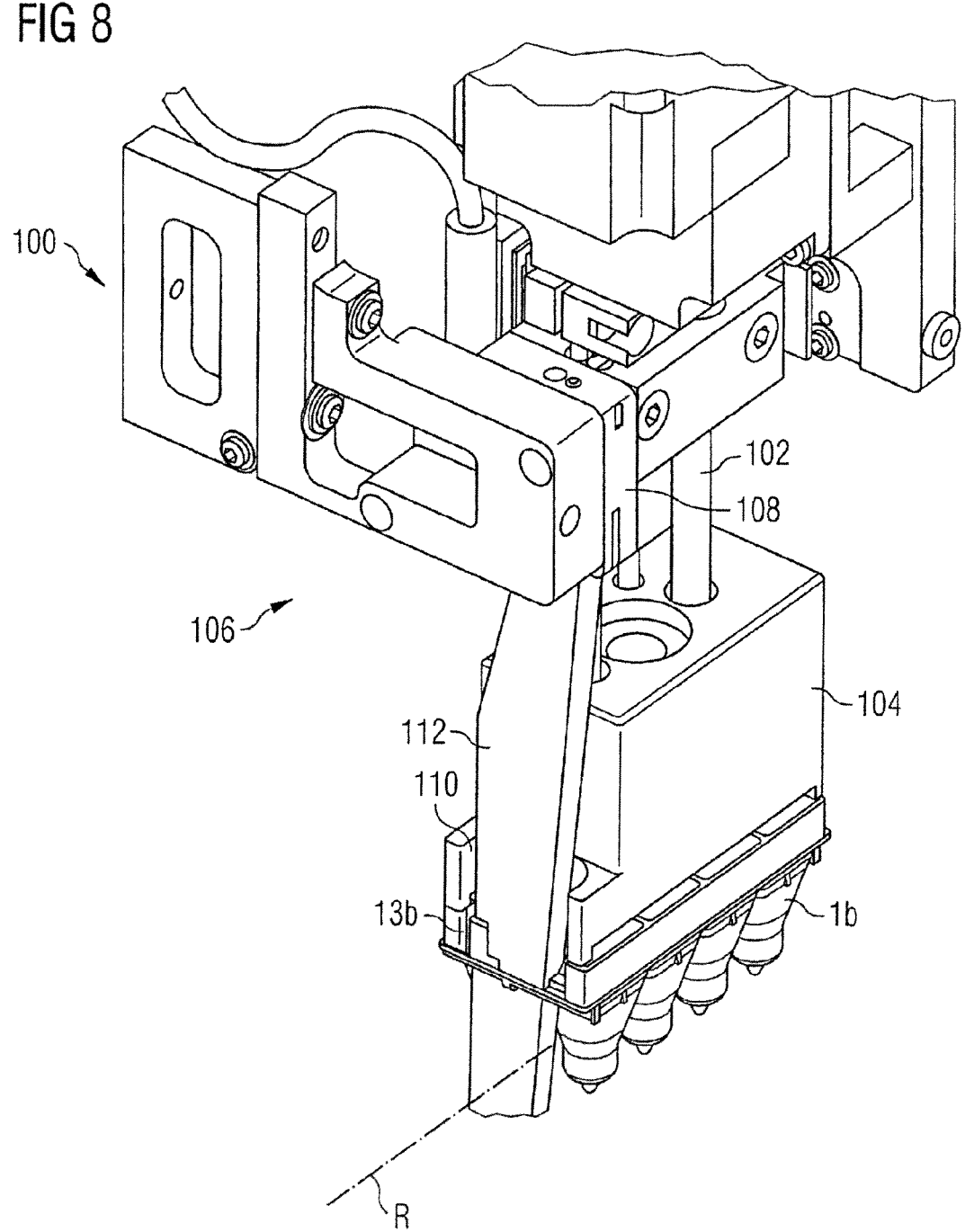
FIG. 8 shows a perspective view of a transporting device with a detection device according to the invention.

FIG. 8 shows a transporting device 100. Further, FIG. 8 shows an object 1b (see FIG. 2a), which is taken by the transporting device. Other objects can be taken and carried by the transporting device 100 as well. The second object be named as an example. The transporting device is configured in such a way that two pins 102 of the transporting unit are inserted in the corresponding openings of object 1b and are brought to engagement with the object. This enables a lifting of the second object. The transporting device cannot only take and transport one object, but also several objects at the same time, which are stacked on top of each other. Above the second object 1b, a weight portion 104 is shown. The weight portion 104 is provided for putting down the objects 1b and is movable along a longitudinal distance. At the side of the transporting device 100, a detection device 106 according to the invention with a laser scanner 108 is arranged. The laser scanner is as described above and can be replaced by a different sensor for distance measurement. The laser scanner 108 is arranged in such a way that it can measure the distance of a detection area arranged on the transversal side 13b of the object 1b. For this purpose, the weight portion 104 can be formed in such a way that it has a recess 110, such that laser beams 112 emitted by the laser scanner 108 are not hindered by the weight portion 104.

In what follows, it will be described how a one-point measurement, i.e., a height measurement at one discrete point of the object, can be used, taken by itself, for determining the number, the spatial position, the presence, the state and/or the type of the object, in particular for a joint determination of several of these parameters.

For determining the height $h_T$ in the 1-point measurement, the detection device 106 can determine the vertical distance between the light sensor and the detection area of the object, and the vertical distance between the light sensor and a reference height R (e.g., the working plate or an upper edge of the locking mechanism of the transporting device 100, see FIG. 8). It is also possible to determine the number, the spatial position, the presence, the state and/or the type of the object directly from the vertical distance between the light sensor and the detection area of the object if the corresponding values are characteristic for the respective parameter.

From the determined height $h_T$, the number of objects located on the working plate or taken by the transporting device can be calculated. This is effected by retrieving the stack height $h_{SO}$ and an identification height d for the identification of objects coming into question, and by comparing with the measured height via the formula $$h_T = (n-1) \times h_{SO} + d,$$

wherein n indicates the number of stacked objects. With a suitable choice of the parameters ($h_{SO}$, d) per object and with a sufficient measurement precision the above formula allows for uniquely determining, from the measured height value $h_T$, the parameter pair ($h_{SO}$, d) and, thus, the type of objects located on the transporting device or on the working plate, as well as the number n of stacked objects.

Example: Two different types of objects come into question, and for object 1 is ($h_{SO}$, d)=(10, 2); for object 2 is ($h_{SO}$, d)=(5,3). Then, from the measured value $h_T$=28, it can be uniquely determined that object 2 is present and n=6 since this is the only solution of the above equation for integer n.

In this way, it can be determined, which objects are located in the process space in which number or were received by the transporting device. This allows for increasing the reliability of the transporting device because the transport process can be supervised and because it can be determined which and how many objects have been taken or disposed by the transporting device.

Further, the detection device 106 arranged at the transporting device 100 can serve to determine the presence of a waste channel 1h or a holder of disposable tips 1i by a 1-point measurement. For that purpose, the transporting device is driven over a predetermined area of the process space or of the process table at which a detection area 9h, 20i of the waste channel 1h or the holder of disposable tips 1i, is assumed. Afterwards, one or more 1-point measurements for determining the distance between the detection device and the detection area are conducted and the result is evaluated by comparing the detected distance with a reference height and by determining, from the comparison, whether a detection area 9h, 20i of the waste channel or of the holder of disposable tips 1i, is present or not.

The detection device does not only serve for identifying the objects taken by the transporting unit 100, but also for inventorying of objects arranged in a process space.

For this, the detection device is led, with objects, such as objects 1a, 1b, 1c, 1d, 1e, 1f, 1g, which have a height profile at a transversal side for discrimination among each other, over the transversal side 13a-g, such that the sensor can generate a height profile by measuring several heights. For example, the detection device can be moved along a line with the help of an actor with path supervision, path measurement device, path regulation and/or path control, such as, e.g., with the help of a step motor, and, per previously defined path section or per defined number of previously defined path sections, one (or more) height measurement is conducted. From these height measurements, a height profile then results along the line, along which the detection device was moved.

The object is identified via this height profile. For this, a signal evaluation is carried out, which is based on the recognition of edges and on the analysis of straight lines. Finding the edges takes place, e.g., with the help of polynomial fitting. The turning point thereby determined is reported as edge position. In particular, the position and type of the edge position is then compared with predetermined values, which are saved in the detection device for every object coming into question, and similarity measure is computed therefrom. This similarity measure is used for determining an object.

Likewise, as on the transporting device, the number of stacked objects (e.g. in a receiving container, see FIG. 2b, or on a process table) can be computed by the detection device 106 via a distance between the object arranged closest to the detection device 106, which has been identified by its height profile arranged at the transversal side 13b, and a reference height, which is, e.g., defined by a working table or the bottom 34 of the receiving container 30.

The line measurement further allows for determining the position and orientation of a drawer according to FIG. 7 by the detecting and precise measuring of a detection area 26j. For this, a detection device arranged at the transporting device or elsewhere is driven to the position at which the recess 26j is assumed. Thereafter, two mutually orthogonal height profiles are generated from the predetermined position (in horizontal x and y direction) by moving the sensor from the predetermined position first in the x direction and then in the y direction whereupon continuing height measurements are executed. Preferably, this is repeated some times, e.g., five times, to obtain the height profiles with high precision. By means of the two mutually orthogonal height profiles, the exact position of two mutually orthogonal edges of the recess 26j can be determined. From the edge positions, the position of upper part of the drawer 1j can be determined. The detected position of the upper part of the drawer can serve as reference point of as reference height for further measurements and/or for processing with the apparatus according to the invention.

Several such recesses can be measured, e.g., to determine also the orientation of the upper part of the drawer 1j besides the position. In this case, it can be determined as well whether the upper part of the drawer 1j has bent or contorted, such that drive paths of, e.g., the transporting device can be adjusted to the exact positioning of the upper part of the drawer 1j.

For inventorying, the detection areas of several objects, which are, e.g., inserted in drawer according to FIG. 7, are detected and the objects are identified. Optionally, receiving openings or receiving areas of the objects are detected by the detection device to determine the equipment of the objects, e.g. with consumables. For example, in the case of a reception of disposable tips as shown in FIGS. 3a-4d and 6, the height values can, e.g., be detected at the individual receiving containers for disposable tips 3c, 3d, 3f, and, from the height values, it can be determined whether a respective disposable tip is present therein.

Figure 9:
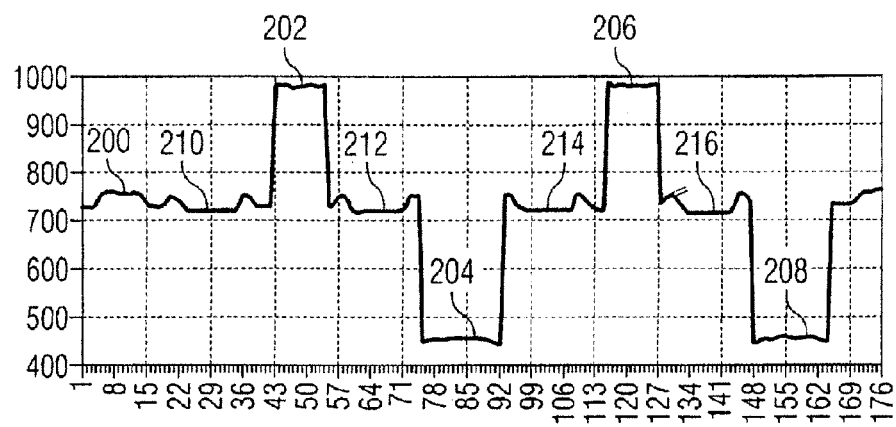
FIG. 9 shows a first graph with a detected height profile according to the invention.

FIG. 9 shows a height profile 200 detected by the detection device, which can be used for inventorying of disposable tips held by a holder of disposable tips (e.g. one of the objects shown in FIG. 3a to FIG. 4d). The abscissa represents the scanned distance of the object (here along a straight line, which passes over eight receiving areas in total for receiving the disposable tips such as 7e in FIG. 4b). The ordinate shows the measured height values. To each receiving area, a respective measured area 210, 202, 212, 204, 214, 206, 216 and 208 is assigned.

In the measurement example of FIG. 9, only every second receiving area out of the eight receiving areas arranged along the measured line are filled with disposable tips. If the sensor detects an invalid value, as, e.g., in the areas 202 and 206, or the bottom in a receiving area, as, e.g., in the areas 204 and 208 of the height profile 200, the detection device or the apparatus concludes that there is no disposable tip arranged in this receiving area. The detected height values deviating upwards can, for example, be generated by reflection or mirroring and represent invalid values (recognizable in that they lie outside of a predetermined tolerance interval). The detected height values deviating downwards can, for example, be generated by detecting a bottom such as a drawer bottom. If, on the other hand, the sensor detects only a small height difference (lying within a predetermined tolerance interval) between the height measurement in the receiving area and in the area surrounding the receiving area, such as the areas 210, 212, 214, and 216, the detection device recognizes by comparison with values deposited in the detection device that a disposable tip is arranged in the respective receiving area. Thus, it can be determined by simple scanning with how many disposable tips and at which receiving areas an object according to the invention is equipped according to FIG. 3a to 4d or 6.

Figure 10:
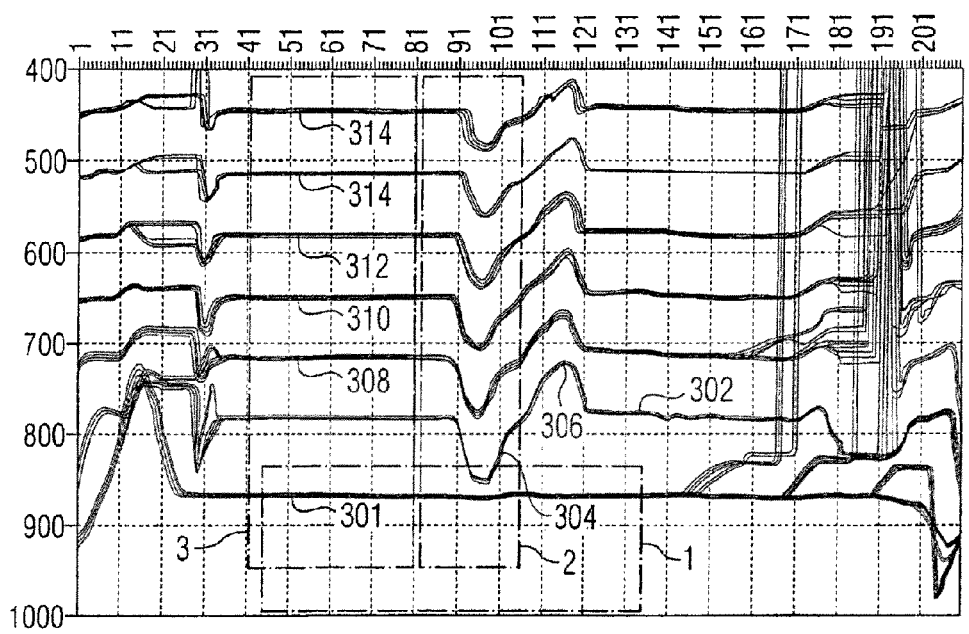
FIG. 10 shows a second graph with several detected height profiles according to the invention.

FIG. 10 shows a second graph with several height profiles detected according to the invention. The abscissa is the distance along one scanning direction S of a line measurement (see, e.g., FIGS. 1, 2). The ordinate represents the detected height.

The measured height profile 301, which has no elevated or lowered area, is obtained by measuring an empty receiving container 30 (see FIG. 2b). It represents the bottom of the receiving container (see the frame referenced by 1 in FIG. 10). From the detected height, it can, in particular, be determined which depth the receiving container 30 has because the bottom thereof is detected.

Furthermore, additional measurement curves of the height profiles 302, 308, 310, 312, 314, 316 are displayed in FIG. 10. The respective measurement curves were obtained by measuring the height profiles of from one (306) to six (316) objects 1a stacked on top of each other, which are stacked in the receiving container, (and were superimposed). This example concerns the measurement values of the height profiles of the first object 1a (see FIG. 1), which has been put in the receiving container 30 (analogous FIG. 2b).

As soon as a first object 1a has been placed, a height profile 302 higher in comparison to the height profile 301 is measured along the transversal side 13a of object 1a, which has a valley 304 and an elevation 306 in the middle of the line. The valley 304 or the elevation 306, are generated by recesses and identification areas, in this case, for example, by the recess 26a and the detection area 20a of the first object 1a. After putting a second, third, fourth, fifth, sixth object a respective third, fourth, fifth, sixth, and seventh height profile 308, 310, 312, 314, 316 is detected, which respectively has a valley and an elevation approximately in the middle of the line. In FIG. 10, e.g., the stack height of the first object can, e.g., be recognized as the difference between the second and third or the third and fourth height profile (different stack heights yield different height profiles; after a single measurement the device may automatically count). From the total height, the number of stacked objects can be determined, either by comparison with values deposited in a database or by applying the formula $h_T=(n-1)\times h_{SO}+d$ (see above). However, should a different object, such as the second object according to the invention, have been put in the receiving container 30, the detected height profile changes. In this case, valleys an elevations in the detected height profile can lie in the area of the frame referenced by 3, instead of in the area of the frame referenced by 2 as in the present case. With the help of this information the detected object can be identified.

The features disclosed in the foregoing description, in the claims and in the drawings can, either singly or in any arbitrary combination, be used for the implementation of the invention in its different embodiments.

The invention claimed is:

1. Apparatus for the purification, processing and/or analysis of biological target molecules with a detection device for detecting at least one object, which comprises at least one detection area,
    wherein the detection device is adapted to detect at least one height value of the detection area and is adapted to determine, from the at least one height value, a spatial position and/or orientation and/or a type and/or a presence and/or a number and/or a state of the at least one object
    wherein the detection device is adapted to determine the difference between the at least one detected height value of the object and a reference height value and to determine a number of stacked objects from the difference and
    wherein the detection device is movably arranged in relation to the object.

2. Apparatus according to claim 1, wherein the detection device is adapted to determine the presence of the object from the at least one detected height value of the object.

3. Apparatus according to claim 1, wherein the detection device is adapted to detect the at least one height values of the object with a one-point measurement.

4. Apparatus according to claim 1, wherein the detection device is adapted to detect at least two height values of at least one detection area of an object.

5. Apparatus according to claim 1, wherein the apparatus is adapted to detect at least two height profiles of an object, wherein the at least two height profiles are particularly arranged on opposing sides of the object, and wherein further the apparatus is particularly adapted to detect the at least two height profiles in opposing directions (S) relative to each other.

6. Apparatus according to claim 1, wherein the detection device, which may generate 3-dimensional images, comprises a radiation source for irradiating the detection area and/or a sensor for measuring the intensity of radiation emanating from the detection area, wherein the radiation source and the sensor are arranged in an angle to a detection area along a line.

7. Apparatus according to claim 1, wherein the apparatus comprises a transporting device for transporting the object.

8. Apparatus according to claim 7, wherein the detection device is arranged close to the transporting device for transporting the at least one object.

9. Apparatus according to claim 7, wherein the at least one height value of the detection area of an object taken by the transporting device is detectable by the detection device, the object being an object of a multitude of, particularly stacked, objects taken by the transporting device.

10. Apparatus according to claim 6, wherein the sensor comprises at least one ultrasonic sensor and/or at least one laser sensor.

11. Apparatus according to claim 6, wherein the radiation source comprises an ultrasonic emitter and/or a laser.

12. Apparatus according to claim 1, wherein the object is a receiving device for receiving material for processing, purification and/or analysis of biological target molecules with at least one identification element, wherein the at least one identification element defines a height profile for identifying the receiving device, wherein the height profile is designed for at least one height measurement and extends at least in sections along a line.

13. An apparatus according to claim 12, wherein the receiving device comprises an outer contour and wherein the height profile extends along the outer contour.

14. An apparatus according to claim 12, wherein the height profile of said receiving device comprises at least one identification area for height measurement, wherein if more than one identification is provided, the identification areas, independently from one another, comprise the same heights or different heights.

15. An apparatus according to claim 14, wherein the receiving device comprises at least two identification areas that are adjacent to each other and/or are arranged with a distance from each other along the height profile.

16. An apparatus according to claim 14, wherein the at least one identification area of said receiving device comprises a length along the line of from substantially 1 mm to substantially 10 mm.

17. An apparatus according to claim 14, wherein the height profile of said receiving device comprises at least two identification areas, which respectively comprise a different length along the line.

18. An apparatus according to claim 14, wherein the at least one identification area of said receiving device comprises a width, transverse to the line, of from substantially 1 mm to substantially 10 mm.

19. An apparatus according to claim 14, wherein at least one, of the at least one identification areas, of said receiving device, is quadrangular.

20. An apparatus according to claim 14, wherein the height profile of said receiving device comprises at least one detection edge, which respectively adjoins an identification area, and which is particularly formed between the identification area and a respective connecting area orthogonal to the identification area.

21. An apparatus according to claim 20, wherein the edge of said receiving device is arranged substantially orthogonal to the longitudinal extension along a line, along which the height profile is detected.

22. An apparatus according to claim 20, wherein two identification areas of said receiving device are adjacent to opposing sides of a connecting area, wherein the two identification areas adjoining the connecting area respectively comprise different heights and optionally different lengths and/or widths, wherein, the connecting area is arranged along the line between the two identification areas.

23. An apparatus according to claim 12, wherein the height profile of said receiving device is substantially symmetric, with respect to a mirror plane orthogonal to the line, which extends, along the outer contour of the receiving device.

24. An apparatus according to claim 12, wherein the height profile of said receiving device is not shaped symmetrically.

25. An apparatus according to claim 23, wherein the identification areas of said receiving device are on both sides of a plane which is substantially orthogonal to the line along which the height profile is detected comprise a different width.

26. An apparatus according to claim 24, wherein the identification areas of said receiving device are on both sides of a plane which is substantially orthogonal to the line along which the height profile is detected comprise a different length and/or height and optionally additionally a different width.

27. An apparatus according to claim 12, wherein the receiving device comprises an outer contour with at least two sides opposing each other, wherein the sides opposing each other each comprise a first or a second, identification element, which are particularly formed axially symmetrically to a middle axis of the receiving device.

28. An apparatus according to claim 12, wherein the receiving device comprises an upper side, from which the material that is to be received is extracted from the receiving device parallel to a middle axis (M), respectively is dispensed in the receiving device, wherein the height profile is arranged such that a height measurement of the height profile is realizable from above.

29. An apparatus according to claim 28, wherein at least one of the identification areas of said receiving device, is arranged orthogonally to the middle axis (M).

30. An apparatus according to claim 12, wherein at least one of the identification areas of said receiving device substantially has the same height as an upper edge of the receiving device.

31. An apparatus according to claim 12, wherein the material that is to be received by the receiving device is selected from the group consisting of consumables, a device part to be protected from direct contact, a material used for processing, purification and/or analysis of biological target molecules, a lysis mixture, binding mixture, buffer mixture, washing mixture, elution mixture and other process mixtures.

32. An apparatus according to claim 12, wherein said receiving device comprises at least one receiving container, closed at one end, for receiving the material.

33. An apparatus according to claim 32, wherein the at least one receiving container comprises a volume of 8 µl to 7000 µl per receiving container.

34. An apparatus according claim 32, wherein said receiving device comprises a plurality of receiving containers wherein the receiving containers are particularly arranged in a matrix arrangement.

35. An apparatus according to claim 12, wherein said receiving device comprises at least one receiving area open on two, opposing sides for receiving the material.

36. An apparatus according to claim 12, wherein said receiving device comprises at least one passage for passing through of a lifting element of a transporting device, wherein the passage extends or the passages particularly extend parallel to the middle axis (M).

37. An apparatus according to claim 12, wherein the receiving device is shaped for an engagement of two receiving devices arranged one on top of the other such that two or more of the receiving devices are stackable in predetermined orientations, such that stacked receiving devices comprise a total height which is smaller than the sum of the single heights of the receiving devices, wherein the receiving devices are particularly stackable such that respective passages of several stacked receiving devices are alignable along a line with respect to each other.

38. An apparatus according to claim 37, wherein the receiving device comprises a stack height of less than 80% of the total height of the receiving device, wherein the stack height is particularly less than substantially 50 mm and/or more than substantially 5 mm.

39. Method for inventorying, position determining and/or orientation determining of objects, which are needed for the automatic processing of a material, which contains biological target molecules, on a corresponding apparatus according to claim 1, in which at least one height value of a detection area of the respective object is detected, and, from the height value, a spatial position and/or an orientation and/or a type and/or a presence and/or a number and/or a state of the respective object is determined on the apparatus.

40. Method according to claim 39, wherein, for determining the spatial position and/or the type and/or the presence and/or the number and/or the state of the object, a one-point measurement for detecting the height value is effected, the value thereby received is compared with correspondingly previously determined data, the result of the comparison is used for controlling the course of the process on the apparatus, and, an indication is optionally given out if the result obtained through the measurement of the height value does not match with the previously determined data.

41. Method according to claim 40, wherein at least two height values, of the detection area are detected, wherein the height profile is arranged along a line, the height values thereby received, are compared with correspondingly previously determined data, the result of the comparison is used for controlling the course of the process on the apparatus, and, an indication is optionally given out if the result obtained through the measurement of the height value, does not match with the previously determined data.

42. Method according to claim 41, wherein at least before the determining of the first height profile at least one calibration height profile along at least one calibration line is detected.

43. Method according to claim 42, wherein the calibration height profile of at least one calibration line is detected, which is located at a position within the device, at which no object is to be detected, and wherein the detected calibration height profile is used as basis for the subsequent height measurements.

44. Method according to claim 42, wherein at least one height profile along at least one calibration line is detected, which extends within the devices orthogonally to a first edge with a defined nominal position, at least one height profile along at least one calibration line is detected, which extends within the devices orthogonally to a second edge with a defined nominal position, wherein the first edge is arranged at right angles to the second edge, the actual positions of the defined edges are determined from the obtained height lines of previous measurements, the actual positions of the edges are compared with their nominal positions, and the information of the comparison between the actual and the nominal positions of the defined edges is used for controlling the further course of the process on the apparatus.

45. Method according to claim 44, wherein the first and/or second edge is, formed by the border of a quadrangular recess or protrusion.

46. Method according to claim 44, wherein, if the discrepancy between the actual and the nominal positions of the defined edges does not exceed a predetermined value, the actual position is used in the course of the process on the apparatus for the definition of the position of other parts or consumables of the apparatus.

47. Method according to claim 44, wherein, when exceeding a predetermined value of the discrepancy between the actual and the nominal positions of the defined edges, an error message is displayed.

48. Method according to claim 39, wherein at least one respective height profile is detected several times along lines parallel to each other, wherein, the lines are laterally displaced with respect to each other.

49. Method according to claim 40, wherein a number of stacked objects is determined from the difference in height between the at least one detected height value of the detection area of the object and a reference height.

50. Method according to claim 40, wherein the type and number of stacked objects is determined by the following formula: $h_T=(n-1) \times h_{so}+d$, wherein $h_T$ is the difference in height between the at least one detected height value of the detection area with the height profile of an object and a reference height, n is the number of stacked objects, $h_{so}$ is the stack height between to neighboring stacked objects, and d is an identification height for identifying the object.

51. Method according to claim 40, wherein at least one object is taken by a transporting device and the at least one height value of the detection area is detected from the received object.

52. Method according to claim 51, wherein a number and/or type of stacked objects is determined while these are taken by the transporting device, and wherein, one or more of the taken and detected objects are deposed by the transporting device.

* * * * *